US006225275B1

(12) United States Patent
Hage et al.

(10) Patent No.: US 6,225,275 B1
(45) Date of Patent: May 1, 2001

(54) METHOD FOR ENHANCING THE ACTIVITY OF AN ENZYME

(75) Inventors: Ronald Hage, Vlaardingen; Jiri Hora, Den Haag; Ton Swarthoff; Robin Stefan Twisker, both of Vlaardingen, all of (NL)

(73) Assignee: Lever Brothers Company, division of Conopco, Inc., New York, NY (US)

( * ) Notice: Subject to any disclaimer, the term of this patent is extended or adjusted under 35 U.S.C. 154(b) by 0 days.

(21) Appl. No.: 09/093,635

(22) Filed: Jun. 4, 1998

(30) Foreign Application Priority Data

Jun. 10, 1997 (EP) .................................................. 97201748

(51) Int. Cl.[7] ................................. C11D 3/28; C11D 3/34; C11D 3/386
(52) U.S. Cl. .......................... 510/374; 510/320; 510/321; 510/392; 510/530; 510/226
(58) Field of Search ........................ 8/401, 137; 510/320, 510/34, 392, 530, 226, 374

(56) References Cited

U.S. PATENT DOCUMENTS

| | | | |
|---|---|---|---|
| 3,978,161 | 8/1976 | Svoboda et al. ........................ 23/253 |
| 4,690,895 | 9/1987 | Farrell ................................... 435/278 |
| 5,445,755 | * 8/1995 | Convents et al. ..................... 252/106 |
| 5,908,472 | * 6/1999 | Vollmond ................................. 8/102 |
| 5,912,405 | * 6/1999 | Schneider et al. ........................ 8/111 |
| 5,948,122 | * 9/1999 | Xu et al. ................................. 8/401 |
| 5,951,714 | * 9/1999 | Hall et al. ................................ 8/102 |

FOREIGN PATENT DOCUMENTS

| | | |
|---|---|---|
| 0087959 | 9/1983 | (EP) . |
| 0717143 | 6/1996 | (EP) . |
| 1057056 | 2/1967 | (GB) . |
| 91/05839 | 5/1991 | (WO) . |
| 424 398 | 3/1992 | (WO) . |
| 94/12619 | 6/1994 | (WO) . |
| 94/12620 | 6/1994 | (WO) . |
| 94/12621 | 6/1994 | (WO) . |
| 97/06244 | 2/1997 | (WO) . |
| 97/11217 | 3/1997 | (WO) . |

* cited by examiner

Primary Examiner—Gregory R. Del Cotto
(74) Attorney, Agent, or Firm—Rimma Mitelman

(57) ABSTRACT

A first aspect of the invention is a process for enhancing the activity of an oxidorecudtase by adding to the enzyme, certain specific compounds which are capable of enhancing the activity of said oxidoreductase enzyme. A second aspect of the invention is an enzymatic bleach composition comprising an oxidoreductase and enhancing compounds.

17 Claims, No Drawings

METHOD FOR ENHANCING THE ACTIVITY OF AN ENZYME

TECHNICAL FIELD

The present invention generally relates to the activation of enzymes by means of enhancing agents. More in particular, the invention is concerned with the activation of oxidoreductases, especially the activation of peroxidase in a process for bleaching fabrics during washing.

BACKGROUND AND PRIOR ART

Oxidoreductases are enzymes concerned with biological oxidation and reduction, and therefore with respiration and fermentation processes. The class of oxidoreductases includes oxidases, laccases (1.10.3), peroxidases (1.11.1.7) and oxygenases. The use of peroxidase and laccase enzymes in a process for the oxidation of a wide variety of substrates is already known. For example, the use of peroxidases for bleaching fabrics during washing has been suggested in EP-A-424 398 (Novo Nordisk). WO-A-91/05839 (Novo Nordisk) describes the inhibition of dye transfer during the wash by means of peroxidase or an enzyme exhibiting oxidase activity on phenolic compounds. The compositions are said to bleach any dissolved textile dye so that no dye can redeposit upon the fabric. U.S. Pat. No. 4,690,895 (Repligen Corporation) discloses the use of a specific peroxidase, namely ligninase, to bleach or decolorize kraft pulp for the production of paper.

It is also known that the activity of oxidoreductases, especially peroxidases, may be increased by the addition of certain organic compounds. The use of such activated enzyme systems for various purposes has also been described, for instance for inhibiting dye transfer in a washing process. The above mentioned WO-A-91/05839 (Novo Nordisk) also describes that the addition of another oxidisable substrate may enhance the enzyme activity. Examples of such oxidisable substrates or "enhancers" are certain phenolic compounds, e.g. 2,4-dichlorophenol.

In three subsequent patent applications (WO-A-94/12619, WO-A-94/12620 and WO-A-94/12621, all Novo Nordisk) it is disclosed that the action of peroxidase in such anti dye-transfer compositions may be enhanced by the addition of a number of aromatic compounds, of which 2,2'-azo-bis-(3-ethylbenzo-thiazoline-6-sulphonate) or ABTS appears to be the preferred compound. However, some of these aromatic compounds may not be attractive as ingredients of detergent compositions for economical or environmental reasons. Furthermore, some of these enhancers like ABTS are, in their oxidised form, dyestuffs themselves. This has the disadvantage that the washed fabrics may be coloured by residual amounts of oxidised ABTS.

WO-A-97/06244 (Ciba) discloses various other compounds as enhancers for peroxidase and laccase systems, such as substituted naphtols, barbituric acids, and substituted coumarins.

Thus, although some of these approaches have been successful to a certain extent, there is still a need for alternative or improved enhancers for the activity of an oxidoreductases. In particular, there is a need for effective enzymatic bleach compositions. It is therefor an object of the present invention to provide such effective alternative or improved oxidoreductase enhancers and enzymatic bleach compositions containing them.

We have now surprisingly found that these and other objects can be achieved by new enzyme enhancers of the invention.

DEFINITION OF THE INVENTION

According to a first aspect of the invention, there is provided a process for enhancing the activity of an oxidoreductase, comprising adding to the enzyme, as an enhancer for the activity of said enzyme, a compound having the formula:

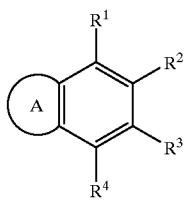

wherein $R^1$–$R^4$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, whereby:

the carbamoyl, sulfamoyl and amino groups may be unsubstituted or substituted once or twice with hydroxy, $C_1$–$C_6$-alkyl, $C_1$–$C_6$-alkoxy, in which $C_1$–$C_6$-group may be saturated or unsaturated, branched or unbranched and may be substituted once or twice with halogen, nitroso, hydroxy, formyl, carboxy, and esters and salts thereof, carbamoyl, sulfo, and esters and salts hereof, sulfamoyl; and the phenyl group may be substituted with once or twice with halogen, nitroso, hydroxy, formyl, carboxy, and esters and salts thereof, carbamoyl, sulfo, and esters and salts hereof, sulfamoyl; and the $C_1$–$C_{20}$ alkyl, $C_1$–$C_8$ alkoxy, carbonyl-$C_1$–$C_6$-alkoxy, and aryl-$C_1$–$C_6$-alkyl groups may be saturated or unsaturated, branched or unbranched, and may be substituted with halogen, hydroxy, nitroso, formyl, carboxy, and esters and salts thereof, carbamoyl, sulfo, and esters and salts thereof, sulfamoyl, nitro, amino, phenyl, aminoalkyl, piperidinyl, piperazinyl, pyrrolidin-2-yl, $C_1$–$C_6$-alkyl, $C_1$–$C_6$-alkoxy;

whereby two of the groups $R^1$–$R^4$ may linked together by any group, and

A is a five or six membered heterocyclic ring which may be optionally substituted with any of the radicals as defined for $R^1$–$R^4$.

According to a second aspect, there is provided an enzymatic bleach composition comprising an oxidoreductase and an enhancer as shown above. According to a third aspect, there is provided a detergent composition comprising the enzymatic bleach composition and which additionally comprises one or more surfactants. According to a fourth aspect, there is provided a process for inhibiting the transfer of a textile dye from one dyed fabric onto the same or another fabric when said fabrics are washed together using the above bleaching composition or a bleaching detergent composition.

DESCRIPTION OF THE INVENTION

A first aspect of the invention is a process for enhancing the activity of an oxidoreductase by adding to the enzyme, certain specific compounds which are capable of enhancing the activity of said oxidoreductase enzyme, the so-called "enhancers". A second aspect of the invention is formed by enzymatic bleach compositions comprising an oxidoreductase and said enhancers.

(a) The oxidoreductase

The enzymatic bleach compositions according to the invention comprise, as a first constituent, an oxidoreductase. The enzyme may either be an enzyme exhibiting peroxidase activity (which is then used together with a source of hydrogen peroxide), or a phenol oxidizing enzyme. A "phenol oxidizing enzyme" is defined for the purpose of the present invention as an enzyme or a system in which an enzyme, by using hydrogen peroxide or molecular oxygen, is capable of oxidizing organic compounds containing phenolic groups. Examples of such enzymes are peroxidases and oxidases. Suitable enzymes are disclosed in EP-A-495 835 (Novo Nordisk). For instance, suitable peroxidases may be isolated from and are producible by plants or microorganisms such as bacteria or fungi. Preferred fungi are strains belonging to the class of the Basidiomycetes, in particular Coprinus, or to the class of Hyphomycetes, in particular Arthromyces, especially *Arthromyces ramosus*. Other preferred sources are Hormographiella sp. or Soybean peroxidase. Other relevant peroxidases are haloperoxidases (U.S. Pat. No. 4,397,192) such as chloride peroxidases, bromide peroxidases and iodide peroxidases. Other potential sources of useful peroxidases are listed in B.C. Saunders et al., Peroxidases, London, 1964, pp 41–43. Also of interest are synthetic or semi-synthetic derivatives and models of such enzymes, such as those comprising iron- or manganese-porphyrin systems, microperoxidases, and iron- or manganese-phthalocyanine compounds, e.g. as described in U.S. Pat. No. 4,077,768, WO-A-91/05858 and WO-A-92/16634. Examples of suitable enzymes exhibiting oxidase activity on phenolic compounds are catechol oxidase and laccase and bilirubin oxidase.

In the context of this invention, laccase and laccase related enzymes contemplate any laccase enzyme comprised by the enzyme classification (EC 1.10.3.2), any catechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.99.1). The laccase enzymes are known from microbial and plant origin. The microbial laccase enzyme may be derived from bacteria or fungi (including filamentous fungi and yeasts) and suitable examples include a laccase derivable from a strain of Aspergillus, Neurospora, e.g. *N. crasse*, Podospora, Botrytis, Collybia, Fomes, Lentinus, Pleurotus, Trametes, (previously called Polyporus), e.g. *T. villosa* and *T. versicolor*, Rhizoctonia, e.g. *R. solani*, Coprinus, e.g. *C. plicatilis* and *C. cinereus*, Psatyrella, Myceliophthora, e.g. *M. thermophylia*, Schytalidium, Phlebia, e.g. *P. radita* (WO-A-92/01046) or Coriolus, e.g. *C. hirsutus* (JP-A-2-238885).

The laccase or the laccase related enzyme may furthermore be one which is reproducible by a method comprising cultivating a host cell transformed with a recombinant DNA vector which carried a DNA sequence encoding said laccase as well as DNA sequence encoding functions permitting the expression of the DNA sequence encoding laccase, in a culture medium under conditions permitting the expression of the laccase enzyme and the recovering the laccase from the culture.

(b) The source of hydrogen peroxide

When peroxidase is used in the enzymatic bleach compositions according to the invention, it is necessary to include a source of hydrogen peroxide. This may be hydrogen peroxide itself, but more stabilised forms of hydrogen peroxide such as perborate or percarbonate are preferred. Especially preferred is sodium percarbonate. Alternatively, one may employ an enzymatic hydrogen peroxide-generating system. The enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. In the latter system, superoxide is generated which decomposes to give hydrogen peroxide. Preferably, however, the combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative *Hansenula polymorpha* strain. (see for example EP-A-244 920 (Unilever)).

If a laccase or laccase-related system is used, the oxidising agent used in the degradation process according to the invention is (molecular) oxygen. This may be supplied conveniently as air or pure oxygen, optionally with the application of pressure. The laccase, or laccase-related system is, however, not limited to solely dioxygen, and any or more of the above bleaching systems may be conveniently employed.

(c) The enhancer

As further ingredient, the compositions of the invention comprise an enhancer compound having the formula:

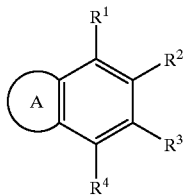

wherein $R^1$–$R^4$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, whereby:
the carbamoyl, sulfamoyl and amino groups may be unsubstituted or substituted once or twice with hydroxy, $C_1$–$C_6$-alkyl, $C_1$–$C_6$-alkoxy, in which $C_1$–$C_6$-group may be saturated or unsaturated, branched or unbranched and may be substituted once or twice with halogen, nitroso, hydroxy, formyl, carboxy, and esters and salts thereof, carbamoyl, sulfo, and esters and salts hereof, sulfamoyl; and
the phenyl group may be substituted with once or twice with halogen, nitroso, hydroxy, formyl, carboxy, and esters and salts thereof, carbamoyl, sulfo, and esters and salts hereof, sulfamoyl; and
the $C_1$–$C_{20}$ alkyl, $C_1$–$C_8$ alkoxy, carbonyl-$C_1$–$C_6$-alkoxy, and aryl-$C_1$–$C_6$-alkyl groups may be saturated or unsaturated, branched or unbranched, and may be substituted with halogen, hydroxy, nitroso, formyl, carboxy, and esters and salts thereof, carbamoyl, sulfo, and esters and salts thereof, sulfamoyl, nitro, amino, phenyl, aminoalkyl, piperidino, piperazinyl, pyrrolidin-2-yl, $C_1$–$C_6$-alkyl, $C_1$–$C_6$-alkoxy;
whereby two of the groups $R^1$–$R^4$ may linked together by any group, and
A is a five or six membered heterocyclic ring which may be optionally substituted with any of the radicals as defined for $R^1$–$R^4$. Preferably, A is a six-membered ring containing at least one nitrogen atom. Especially preferred enhancers are hydroxy quinolines and hydroxyisoquinolines, whereby 3-hydroxy quinoline (3HQ), 6-hydroxy quinoline (6HQ) and 7-hydroxy quinoline (7HQ), 3-hydroxy-isoquinoline (3-isoHQ), 7-hydroxy-isoquinoline (7-isoHQ) are the most preferred. Other preferred enhancers are nitroso-derivatives of hydroxy quinoline and hydroxy-isoquinoline, such as 8-nitroso-7-hydroxy-isoquinoline, 5-nitroso-8-hydroxyquinoline and 7-nitroso-8-hydroxyquinoline.

Alternatively, A may be a sulphur containing five-membered ring. In that case, hydroxy benzothiophenes are preferred, such as 5-hydroxy benzothiophene (5HB). Another preferred group of enhancers are the benzothiazoles, 2-methyl-5-benzothiazolol (2MB) being especially preferred.

(d) Applications

The process and the bleach composition of the present invention may in principle be applied in all situations where oxidoreductases are now used or have been suggested, such as pulp bleaching in the paper industry, waste water treatment and fabric washing. The invention is of particular use to formulate detergent compositions which are capable of bleaching fabrics during washing, but also to formulate enzymatic anti dye-transfer compositions, even at alkaline pH and in the presence of proteolytic enzymes. The enzymatic bleach compositions and the detergent compositions of the invention may take any suitable physical form, such as a powder, an aqueous or non-aqueous liquid, a paste or a gel. However, granular detergents (powders) are preferred.

The enzymatic bleach compositions of the invention comprise about 0.001 to 50 milligrams of active enzyme per gram of detergent composition. Preferably, they comprise 0.001 to 5 milligrams of active enzyme protein per gram of detergent composition, more preferably 0.005 to 1.0 milligrams per gram. More conveniently, the amount of oxidoreductase enzyme is expressed as units of enzyme activity. The amount of peroxidase enzyme can be usefully expressed in ABTS (2,2'-azino-bis(3-ethylbenzothiazoline-6-sulphonic acid) units. One ABTS unit represents the amount of enzyme which oxidizes ABTS, resulting in an increase of 1 unit optical density at 418 nm in one minute. Conditions for the activity assay are 2 mM ABTS, 1 mM $H_2O_2$, 20 mM Tris, pH 9. The amount of laccase can also be expressed in ABTS units, using slightly different conditions because of the pH optimum of laccase (2 mM ABTS in 20 mM sodium phosphate buffer pH 6.0 at 25° C.).

The oxidoreductases used in the present invention can usefully be added to detergent compositions in any suitable form, i.e. the form of a granular composition, a liquid or a slurry of the enzyme, with carrier material (e.g. as in EP-A-258 068 and the Savinase (TM) and Lipolase (TM) products of Novo Nordisk), or a coating. A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

If desired, a slow-release coating may be applied to the granulate of the oxidoreductase. By means of such coatings, it is possible to achieve the controlled release of the enzyme when the granulate is introduced in the washing liquor. Preferred slow-release materials are compounds that are substantially insoluble in water.

Examples of such materials include long-chain fatty acid mono, di-, triesters of glycerol, ethoxylated fatty alcohols, latexes, waxes, tallow, hydrogenation tallow, partially hydrolyzed tallow, hydrocarbons having a melting point in the range of 50–80° C.

(e) Surfactants

When used to formulate bleaching detergent compositions, the compositions of the invention will usually contain, one or more detergent-active compounds (surfactants) which may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and nonionic compounds. The detergent composition may comprise both nonionic and anionic surfactant, it is preferred if the ratio of nonionic surfactant to anionic surfactant is at least 1 to 3, more preferably at least 1 to 1. It is especially preferred if the detergent composition is substantially free of anionic surfactant, in particular linear alkyl benzene sulphonate. Anionic surfactants are well-known to those skilled in the art. Examples include alkylbenzene sulphonates, particularly linear alkylbenzene sulphonates having an alkyl chain length of $C_8$–$C_{15}$; primary and secondary alkylsulphates, particularly $C_8$–$C_1S$ primary alkyl sulphates; alkyl ether sulphates; olefin sulphonates; alkyl xylene sulphonates; dialkyl sulpho-succinates; and fatty acid ester sulphonates. Sodium salts are generally preferred.

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 (and preferably 3 to 7) moles of ethylene oxide per mole of alcohol. Non-ethoxylated nonionic surfactants include alkylpolyglycosides, glycerol monoethers, and polyhydroxyamides (glucamide).

The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60% by weight, for example, in a composition for washing fabrics by hand. In compositions for machine washing of fabrics, an amount of from 5 to 40% by weight is generally appropriate. Detergent compositions suitable for use in most automatic fabric washing machines generally contain anionic non-soap surfactant, or nonionic surfactant, or combinations of the two in any ratio, optionally together with soap.

(f) Detergency Builders

The enzymatic bleach compositions of the invention will generally also contain one or more detergency builders. This detergency builder may be any material capable of reducing the level of free calcium ions in the wash liquor and will preferably provide the composition with other beneficial properties such as the generation of an alkaline pH, the suspension of soil removed from the fabric and the suspension of the fabric-softening clay material. The total amount of detergency builder in the compositions will suitably range from 5 to 80%, preferably from 10 to 60% by weight. Inorganic builders that may be present include sodium carbonate, if desired in combination with a crystallisation seed for calcium carbonate, as disclosed in GB-A-1 437 950

(Unilever); crystalline and amorphous aluminosilicates, for example, zeolites as disclosed in GB A 1 473 201 (Henkel), amorphous aluminosilicates as disclosed in GB-A-1 473 202 (Henkel) and mixed crystalline/amorphous aluminosilicates as disclosed in GB-A-1 470 250 (Procter & Gamble); and layered silicates as disclosed in EP-B-164 (Hacksawed). Inorganic phosphate builders, for example, sodium orthophosphate, pyrophosphate and tripolyphosphate, may also be present, but on environmental grounds those are no longer preferred.

The detergent compositions of the invention preferably contain an alkali metal, preferably sodium, alumino-silicate builder. Sodium aluminosilicates may generally be incorporated in amounts of from 10 to 70% by weight (anhydrous basis), preferably from 25 to 50% by weight. The alkali metal aluminosilicate may be either crystalline or amorphous or mixtures thereof, having the general formula:

0.8–1.5 $Na_2O.Al_2O_3.0.8$–6 $SiO_2$

These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB-A-1 429 143 (Proctor & Gamble). The preferred sodium aluminosilicates of this type are the well-known commercially available zeolites A and X, and mixtures thereof. The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP-A-384 070 (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20. Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30% by weight, preferably from 10 to 25% by weight, and acrylic polymers, more especially acrylic/maleic copolymers, suitably used in amounts of from 0.5 to 15%, preferably from 1 to 10% by weight. Builders, both inorganic and organic, are preferably present in the form of their alkali metal salt, especially their sodium salt.

(g) Other ingredients.

The enzymatic bleach compositions of present invention may also comprise, in further embodiments, combinations with other enzymes and other constituents normally used in detergent systems, including additives for detergent compositions. Such other components can be any of many known kinds, for example enzyme stabilisers, lather boosters, soil suspending agents, soil-release polymers, hydrotropes, corrosion inhibitors, dyes, perfumes, silicates, sequestrants, optical brighteners, suds depressants, germicides, anti tarnishing agents, opacifiers, fabric softening agents, buffers and the like.

The bleach system may contain apart from the hydrogen peroxide source, as disclosed above, also a peracid-forming bleach activator such as tetraacetyl-ethylene-diamine (TAED) or N,N-phthaloylaminoperoxy caproic acid (PAP). Alternatively, inorganic peroxyacids like potassium monopersulphate (MPS) may be employed. Alkyl hydroperoxides are another class of peroxy bleaching compounds. Examples of these materials include t-butyl hydroperoxide and cumene hydroperoxide. Optionally, bleach catalysts can be included. Such compounds are well known in the art and include, for example, manganese-based catalysts as disclosed in U.S. Pat. No. 5,246,621, U.S. Pat. No. 5,244,594, U.S. Pat. No. 5,194,416, U.S. Pat. No. 5,114,606, EP-A-458 397 and EP-A-458 397 or the iron-based catalysts as disclosed in WO-A-95/34628.

Examples are described in GB-A-1 372 034 (Unilever), U.S. Pat. No. 3,950,277, U.S. Pat. No. 4,011,169, EP-A-179 533 (Procter & Gamble), EP-A-205 208 and EP-A-206 390 (Unilever), JP-A-63 078000 (1988), and Research Disclosure 29056 of June 1988. The formulation of detergent compositions according to the invention can be also illustrated by reference to the Examples D1 to D14 of EP-A-407 225 (Unilever).

Special advantage may be gained in such detergent compositions wherein a proteolytic enzyme or protease is also present. Proteases for use in the enzymatic bleach compositions may include subtilisins of, for example, BPNI type or of many of the types of subtilisin disclosed in the literature, some of which have already been proposed for detergents use, e.g. mutant proteases as described in for example EP-A-130 756 or EP-A-251 446 (both Genentech), U.S. Pat. No. 4,760,025 (Genencor), EP-A-214 435 (Henkel), WO-A-87/04661 (Amgen), WO-A-87/05050 (Genex), Thomas et al. (1986) Nature 5, 316, and 375–376 and in J.Mol.Biol. (1987) 193, 803–813, Russel et al. (1987) Nature 328, 496–500, and others.

Furthermore, certain polymeric materials such as polyvinyl pyrrolidones typically having a molecular weight of 5,000 to 20,000 are useful ingredients for preventing the transfer of labile dye stuffs between fabrics during the washing process. Especially preferred are ingredients which also provide colour care benefits. Examples thereof are polyamide-N-oxide containing polymers.

The invention will now be further illustrated in the following non-limiting Examples.

EXAMPLE 1

The enhancers used in the following examples have the following formulae:

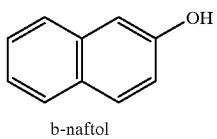

b-naftol

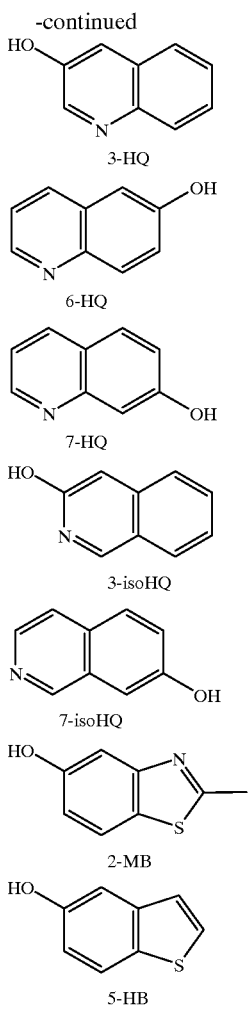

3-HQ

6-HQ

7-HQ 3-isoHQ 7-isoHQ

2-MB

5-HB

The oxidation of Acid Red 88 (AR88) is monitored spectrophotometrically at 500 nm in a spectrophotometer. The reagents are added, using a pipette, in the following order, to a 1-cm cuvette: aqueous carbonate buffer pH 9 (20 mM), ORB (60 μM), enhancer (100 μM), hydrogen peroxide (250 μM) and peroxidase enzyme (*Arthromyces ramosus* peroxidase from Sigma, P4794); 0.6 units/ml). The reaction was carried out for 30 minutes at room temperature. The difference in absorbance between t=0 and t=30 min is a measure of the enhancing activity of the system tested.

| Enhancer | start | end | Δ Abs. | % |
|---|---|---|---|---|
| β-naftol | 1.20 | 0.98 | 0.22 | 18 |
| 3-HQ | 1.25 | 0.94 | 0.31 | 25 |
| 6-HQ | 1.15 | 0.38 | 0.77 | 67 |
| 7-HQ | 1.26 | 0.79 | 0.47 | 37 |
| 7-isoHQ | 1.23 | 0.25 | 0.98 | 80 |
| 2-MB | 1.26 | 0.08 | 1.18 | 94 |
| 5-HB | 1.20 | 0.81 | 0.39 | 33 |

EXAMPLE 2

The oxidation of Reactive Black 5 (RB5) is monitored spectrophotometrically at 590 nm in a spectrophotometer. The reagents are added, using a pipette, in the following order, to a 1-cm cuvette: aqueous carbonate buffer pH 9 (20 mM), RB5 (60 EM), enhancer (100 FM) and peroxidase enzyme (*Arthromyces ramosus* peroxidase from Sigma, P4794); 6 units/ml). The reaction was carried out for 30 minutes at room temperature. The difference in absorbance between t=0 and t=30 min is a measure of the enhancing activity of the system tested.

RB5 [590 nm]: 25° C., pH 9, 30 min.
ARP [60 u/ml], $H_2O_2$ [250 μM], DG26 [60 μM], Enhancers [100 μM]

| Enhancer | start | end | Δ Abs. | % |
|---|---|---|---|---|
| β-naftol | 1.13 | 0.95 | 0.18 | 16 |
| 3-HQ | 1.18 | 0.38 | 0.80 | 68 |
| 6-HQ | 1.15 | 0.40 | 0.75 | 65 |
| 7-HQ | 1.32 | 0.52 | 0.80 | 61 |
| 3-isoHQ | 1.23 | 0.76 | 0.47 | 38 |
| 7-isoHQ | 1.18 | 0.59 | 0.59 | 50 |
| 2-MB | 1.00 | 0.50 | 0.50 | 50 |
| 5-HB | 1.18 | 0.07 | 0.22 | 19 |

EXAMPLE 3

The oxidation of Direct Green 26 (DG26) is monitored spectrophotometrically at 610 nm in a spectrophotometer. The reagents are added, using a pipette, in the following order, to a 1-cm cuvette: aqueous carbonate buffer pH 9 (20 mM), DG26 (60 μM), enhancer (100 μM) and peroxidase enzyme (*Arthromyces ramosus* peroxidase from Sigma, P4794); 6 units/ml). The reaction was carried out for 30 minutes at room temperature. The difference in absorbance between t=0 and t=30 min is a measure of the enhancing activity of the system tested.

DG26 [610 nm]: 25° C., pH 9, 30 min.
ARP [60 u/ml], $H_2O_2$ [250 μM], DG26 [60 μM], Enhancers [100 μM]

| Enhancer | start | end | Δ Abs. | % |
|---|---|---|---|---|
| β-naphtol | 1.50 | 1.47 | 0.03 | 2 |
| ABTS | 1.60 | 0.54 | 1.06 | 66 |
| 3-HQ | 1.43 | 0.80 | 0.63 | 56 |
| 6-HQ | 1.53 | 1.00 | 0.53 | 35 |
| 7-HQ | 1.39 | 0.69 | 0.70 | 50 |
| 7-isoHQ | 1.35 | 0.61 | 0.74 | 45 |
| 2-MB | 1.50 | 1.35 | 0.20 | 13 |

It can be seen that the enhancers 3HQ, 6HQ, 7HQ, 3-isoHQ, 7-isoHQ, 2MB, and 5HB are significantly better enhancers to bleach ORB and RB5 homogeneously than β-naftol. This illustrates the positive influence of the hetero atom in the para position to the hydroxyl group in the aromatic rings. Also on DG26 with 3HQ, 6HQ, 7HQ, 7-isoHQ, and 2MB a positive effect on the bleaching activity with respect to β-naftol is found.

EXAMPLE 4

The laccase activity is measured on a spectrophotometer with 2 mM ABTS in 20 mM sodium phosphate buffer pH 6.0 at 25° C. The oxidation of Reactive Black 5 (RB5) is monitored spectrophotometrically at 575 nm in a spectrophotometer. The reagents are added, using a pipette, in the following order, to a 1-cm cuvette: aqueous tris buffer pH 9 (20 mM) or sodium phosphate buffer pH 6.0 (20 mM), RB5 (67 μM), enhancer (67 μM), and laccase (*Polyporus pinsitus*, 30 units/ml). The reaction was carried for 3 hours at room temperature. The difference in absorbance between t=0 and t=3 hours is a measure of the enhancing activity of the system tested. The results are shown in the table.
RB5 [575 nm]: 25° C., pH 6.0 and 9.0, 3 h.

Laccase [30 u/ml], RB5 [67 μM], Enhancers [67 μM]. The values listed are the decrease in absorbance at 605 nm after 3 h.

| Enhancer | pH 6.0 | pH 9.0 |
|---|---|---|
| blank | 0.07 | 0.10 |
| ABTS | 0.99 | 0.23 |
| 6-HQ | 0.39 | 0.18 |
| 7-HQ | 0.21 | 0.14 |

EXAMPLE 5

The oxidation of Direct Green 26 (DG26) is monitored spectrophotometrically at 605 nm in a spectrophotometer. The reagents are added, using a pipette, in the following order, to a 1-cm cuvette: aqueous tris buffer pH 9 (20 mM) or sodium phosphate buffer pH 6.0 (20 mM), DG26 (67 μM), enhancer (67 μM), and laccase (*Polyporus pinsitus*, 30 units/ml). The reaction was carried for 3 hours at room temperature. The difference in absorbance between t=0 and t=3 h is a measure of the enhancing activity of the system tested. The results are shown in the table.
DG26 [605 nm]: 25° C., pH 6.0 and 9.0, 3 h.

Laccase [30 u/ml], DG6 [67 μM], Enhancers [67 μM]. The values listed are the decrease in absorbance at 605 nm after 3 h.

| Enhancer | pH 6.0 | pH 9.0 |
|---|---|---|
| blank | 0.06 | 0.07 |
| ABTS | 0.57 | 0.44 |
| 6-HQ | 0.29 | 0.15 |
| 7-HQ | 0.14 | 0.09 |

What is clamed is:

1. Process for enhancing the activity of an oxidoreductase, comprising adding to the enzyme, as an enhancer for the activity of said enzyme, a compound having the formula:

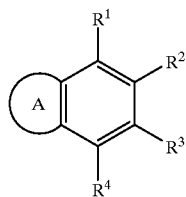

wherein $R^1$–$R^4$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, whereby:

the carbamoyl, sulfamoyl and amino groups may be unsubstituted or substituted once or twice with hydroxy, $C_1$–$C_6$-alkyl, $C_1$–$C_6$-alkoxy, in which $C_1$–$C_6$-group may be saturated or unsaturated, branched or unbranched and may be substituted once or twice with halogen, nitroso, hydroxy, formyl, carboxy, and esters and salts thereof, carbamoyl, sulfo, and esters and salts hereof, sulfamoyl; and the phenyl group may be substituted with once or twice with halogen, nitroso, hydroxy, formyl, carboxy, and esters and salts thereof, carbamoyl, sulfo, and esters and salts hereof, sulfamoyl; and the $C_1$–$C_{20}$ alkyl, $C_1$–$C_6$-alkoxy, carbonyl-$C_1$–$C_6$-alkoxy, and aryl-$C_1$–$C_6$-alkyl groups may be saturated or unsaturated, branched or unbranched, and may be substituted with halogen, hydroxy, nitroso, formyl, carboxy, and esters and salts thereof, carbamoyl, sulfo, and esters and salts thereof, sulfamoyl, nitro, amino, phenyl, aminoalkyl, piperidino, piperazinyl, pyrrolidin-2-yl, $C_1$–$C_6$-alkyl, $C_1$–$C_6$ alkyl, $C_1$–$C_6$-alkoxy;

whereby two of the groups $R^1$–$R^4$ may be linked together by any group, and

A is selected from the group consisting of a six-membered ring containing at least one nitrogen atom and a sulphur containing five-membered ring which may be optionally substituted with a hydroxy group.

2. Process according to claim 1, wherein the enhancer is a hydroxy quinoline.

3. Process according to claim 2, wherein the enhancer is 3-hydroxy quinoline, 6-hydroxy quinoline or 7-hydroxy quinoline.

4. Process according to claim 1, wherein the enhancer is a hydroxy benzothiophene.

5. Process according to claim 1, wherein the enhancer is 5-hydroxy benzothiophene.

6. Process according to claim 1, wherein the enhancer is a benzothiazol.

7. Process according to claim 1, wherein the enhancer is 2-methyl-5-benzothiazolol.

8. An enzymatic bleach composition comprising: (a) an oxidoreductase (b) an enhancer according to claim 1.

9. An enzymatic bleach composition according to claim 8, comprising (a) an enzyme exhibiting peroxidase activity and a source of hydrogen peroxide.

10. An enzymatic bleach composition according to claim 8, wherein the source of hydrogen peroxide is an alkali metal percarbonate.

11. An enzymatic bleach composition according to claim 8, wherein the amount of hydrogen peroxide us from 0.001 to 10 mM.

12. An enzymatic bleach composition according to claim 8, wherein said oxidoreductase is a phenol oxidising enzyme.

13. An bleaching detergent composition comprising an enzymatic bleach composition according to claim 8 and one or more surfactants.

14. A bleaching detergent composition according to claim 13, further comprising a proteolytic enzyme.

15. A bleaching detergent composition according to claim 13, in which the proteolytic enzyme is a subtilisin protease.

16. A bleaching detergent composition according to claim 13, in the form of an granular detergent composition.

17. Process for inhibiting the transfer of a textile dye form one dyed fabric onto the same or another fabric when said fabrics are washed together using a bleaching composition according to claim 8.

* * * * *